United States Patent
Müller (10) Patent No.: US 8,685,695 B2
(45) Date of Patent: Apr. 1, 2014

(54) METHOD FOR PRODUCING A MIXTURE OF BACTERIOPHAGES AND THE USE THEREOF IN THE THERAPY OF ANTIBIOTIC-RESISTANT STAPHYLOCOCCI

(75) Inventor: Robert F Müller, Bornheim (DE)

(73) Assignee: PhytoLine GmbH, Viersen (DE)

( * ) Notice: Subject to any disclaimer, the term of this patent is extended or adjusted under 35 U.S.C. 154(b) by 498 days.

(21) Appl. No.: 12/933,234

(22) PCT Filed: Mar. 13, 2009

(86) PCT No.: PCT/EP2009/001845
§ 371 (c)(1), (2), (4) Date: Sep. 17, 2010

(87) PCT Pub. No.: WO2009/115245
PCT Pub. Date: Sep. 24, 2009

(65) Prior Publication Data
US 2011/0014157 A1    Jan. 20, 2011

(30) Foreign Application Priority Data
Mar. 20, 2008 (EP) .................................. 08005273

(51) Int. Cl.
*C12N 7/00* (2006.01)
*A01N 63/00* (2006.01)

(52) U.S. Cl.
USPC ...................... 435/235.1; 424/93.6

(58) Field of Classification Search
None
See application file for complete search history.

(56) References Cited

U.S. PATENT DOCUMENTS

2004/0247569 A1 * 12/2004 Morris et al. ................ 424/93.6

FOREIGN PATENT DOCUMENTS

WO    WO 2006/047870 A    5/2006
WO    WO 2007/148919 A    12/2007

OTHER PUBLICATIONS

Capparelli et al., Antimicrobial Agents and Chemotherapy, 2007, 51(8):2765-2773.*
O'Flaherty et al., Environmental Microbiology, 2005, 71(14):1836-1842.*
Moore et al., Journal of Clinical Microbiology, 2001, 39 (8):2760-2767.*
Samra et al., Eur J Clin Microbiol Infect Dis, 2001, 20 :425-427.*
O'Flaherty, et al. "Potential of the polyvalent Anti-*Staphylococcus* bacteriophage K for control of antibiotic-resistant staphylococci from hospitals," Applied and Environmental Microbiology, vol. 71 (4), pp. 1836-1842 (2005).
Capparelli, et al. "Experimental phage therapy against *Staphylococcus aureus* in mice," Antimicrobial Agents and Chemotherapy, vol. 51 (8), pp. 2766-2768 (2007).
Rashel, et al. "Efficient elimination of multidrug-resistant *Staphylococcus aureus* by cloned lysine derived from bacteriophage phi MR11," Journal of Infectious Diseases, vol. 196 (8), pp. 1237-1247 (2007).

* cited by examiner

*Primary Examiner* — Nicole Kinsey White
(74) *Attorney, Agent, or Firm* — Chalin A. Smith; Smith Patent Consulting (57) ABSTRACT

The invention relates to a method for producing a mixture of bacteriophages, wherein at least two different bacteriophage strains have been reproduced separately, wherein a *staphylococcus* strain is grown in an preculture with each of strains of a bacteriophage that can lyse *staphylococci* and is then further reproduced in a main culture, and is then purified, and the different strains are then mixed, wherein the mixture of bacteriophages used comprises at least two different serotypes of bacteriophages that lyse specifically bacteria of the species *Staphylococcus*.

9 Claims, 1 Drawing Sheet

METHOD FOR PRODUCING A MIXTURE OF BACTERIOPHAGES AND THE USE THEREOF IN THE THERAPY OF ANTIBIOTIC-RESISTANT STAPHYLOCOCCI

This application corresponds to the national phase of International Application No. PCT/EP2009/001845 filed Mar. 13, 2009, which, in turn, claims priority to European Patent Application No. 08.005273.1 filed Mar. 20, 2008, the contents of which are incorporated by reference herein in their entirety.

Bacterial infections cause many diseases, some of which are fatal. Many of these bacterial infections have been successfully combated by the development of antibiotics. However, the wholesale use of different antibiotics has resulted in the appearance of bacteria which are often resistant not merely to one antibiotic but to many antibiotics. Such highly resistant strains of bacteria are, to an increasing degree, causing serious problems, the very area where this is true being in hospitals, because it is there that patients can be infected with such strains even by the treatments administered by physicians. If these strains are resistant to the majority of the antibiotics which are normally used, this may give rise to extremely serious illnesses which not infrequently end in death.

Within the scope of the present invention, recourse is had to an alternative means of combating bacteria. In the same way as there are viruses which attack plants and animals and in so doing not infrequently cause severe illnesses, so too are there viruses which attack specifically bacteria. These viruses are called bacteriophages. They are usually specific to given types of bacteria and often bind to those regions of the bacterial cell wall at which the absorption of nutrients (e.g. sugars and the like) usually takes place. The adsorption of the bacteriophages at the bacterial cell wall having taken place, the bacteriophages inject their nucleic acid into the bacterium. The nucleic acid reproduces in the bacterium and bacteriophage-specific proteins are formed. When enough copies of the nucleic acid of the bacteriophage and sufficient bacteriophage protein are present in the bacterial cell, they lyse the bacterial cell and large numbers of the bacteriophages which have formed are released into the surroundings. The cycle of infection can then begin again.

The use of bacteriophages for the therapy of given sicknesses has been known for a number of decades. This method of combating bacteria has been developed particularly in Eastern European countries. Described in WO 2004/052274 is a method of producing bacteriophage compositions which can be used in the therapy of bacterial infections and in particular ones which are caused by *Pseudomonas aeruginosa*. The culturing of bacteriophages is carried out in this case in a semi-solid culture medium. WO 97/39111 describes a method of producing bacteriophages which have a wide spectrum of hosts and the use of these bacteriophages in therapy. Disclosed in WO 01/50866 is the use of a cocktail of bacteriophages for destroying bacteria on various solid surfaces, such for example as in operating rooms or even in facilities for housing livestock and in slaughterhouses.

US 2004/0247569 describes pharmaceutical compositions containing bacteriophages which are able to inactivate various antibiotic-resistant bacteria such as *Enterococcus, Staphylococcus aureus, Pseudomonas* and others. WO 2006/047870 describes stabilised bacteriophage compositions which are adsorbed on a matrix. O'Flaherty et al., Applied and Environmental Microbiology [2005], pp. 1836-1842 describe the anti-*staphylococcus* bacteriophage K and its use for controlling antibiotic-resistant *staphylococci* from hospitals. WO 2007/148919 describes a bacteriophage specific to *Staphylococcus aureus* and the use thereof in combating infections. Capparelli et al., Antimicrobial agents and Chemotherapy [2007], pp. 2675-2773 describe the bacteriophage $M^{Sa}$ and its use against *Staphylococcus aureus* in the mouse model. Rashel et al., JID [2007], pp. 1237-1247 describe the cloning of endolysin, an enzyme which breaks down peptidoglycan, from the bacteriophage ΦMR11.

The present invention relates to a method for producing a mixture of bacteriophages wherein a *staphylococcus* strain is first grown in a preculture with a bacteriophage that can lyse *staphylococci* and is then further reproduced in a main culture. A plurality of such bacteriophages is then combined to form a mixture.

The mixture of bacteriophages which is used comprises at least two, preferably at least three, different serotypes of bacteriophages which lyse specifically bacteria of the species *Staphylocuccus*. Bacteriophage strains which are preferably used come from the phage classes Myoviridae and Podoviridae.

An important aspect of the invention is the fact that a plurality of different bacteriophages is used which all have the common property that they can lyse *staphylococci*. In particular, the bacteriophages which are used must lyse *staphylococci* which are involved in sicknesses and conditions which are pathogenic to humans and/or animals. As a particular preference, the bacteriophages which are used in accordance with the invention lyse *staphylococci*, and in particular strains of *Staphylococcus aureus*, which are resistant to antibiotics and in particular to methicillin. It is an important aspect of the present invention that a plurality of different bacteriophages is present in the mixture of bacteriophages. These may be bacteriophages which lyse specifically strains of *Staphylococcus aureus* but they may also be bacteriophages which lyse other types of bacteria, although such strains are preferably only used in addition to a mixture of bacteriophages which belong to at least two different serotypes.

The bacteriophages which are used in the method employed in accordance with the invention may be either precisely characterised bacteriophages or may originate from a wild isolate. For this purpose, using normal methods of bacteriophage isolation and starting from a suitable source, the bacteriophages are first increased by joint growth with strains of *staphylococcus* and are then used in the method according to the invention.

In the method according to the invention, a methicillin-sensitive strain of *Staphylococcus aureus* is preferably used for the reproduction of the bacteriophages for safety reasons.

It is precisely in problematic infections in hospitals that methicillin-resistant strains of *Staphylococcus aureus*, often abbreviated to MRSA, are frequently encountered. However, what is preferably used for the reproduction of the bacteriophage mixture is a methicillin-sensitive strain of *Staphylococcus aureus* (MSSA). Under the Budapest Treaty, the preferred strain was deposited at the German Collection of Microorganisms and Cell Cultures [Deutsche Sammlung von Mikroorganismen and Zellkulturen GmbH or "DSMZ"], located at Inhoffenstrasse 7B, 38124 Braunschweig (Brunsick), Germany, on Jul. 11, 2006 under the accession number DSM 18421.

A particularly important advantage of the strain of *Staphylococcus aureus* which is used in accordance with the invention for the reproduction of the bacteriophages is that a plurality of the following virulence factors is not present in this strain. These are the following toxin determinants which are located on transferrable elements:

tst: 161/93
sea: 619/93
seb: 62/92
sec: 1229/93
sed: 1634/93
see: FRJ918
eta: 1437/100
eta, etb: 1004/00
lukS-lukF: 3925/02
cna: 2773/03
seg: N315
seg and seh: 2773/03.

In a preferred embodiment the above-mentioned virulence factors are not present, in their entirety, in the strain used.

Because of this, virulence factors cannot be transferred to the bacteriophages from the strain used for reproduction and in this respect the reproduction of the bacteriophages is particularly safe.

Another advantage of the strain which is used for reproduction in accordance with the invention is that the properties of the bacteriophages which are reproduced in the strain do not change even after a plurality of passages.

For the production according to the invention of the mixture of bacteriophages, a preculture of the strain of *Staphylococcus aureus* which is used is grown as the first step. When the bacteria have reached a suitable optical density, the bacteriophage to be reproduced is added, a bacteria-to-bacteriophage ratio of approximately $10^5$ to $10^2$ bacteria to 1 phage being set in the preculture.

The preculture, together with the bacteriophages, is then grown until such time as the lysing of the bacteria begins. The preculture containing the bacteriophages is then added to a main culture of *staphylococci*, the ratio which is set preferably being one where the bacteria are present in a considerable excess. A particular preference is a range of approximately from 50 to 1000 bacteria per bacteriophage. What is achieved by this excess is that all the bacteriophages present in the preculture find a suitable bacterium in which they can reproduce.

The ratio of bacteriophages to bacteria is also referred to as what is known as the MOI (multiplicity of infection) value. In a preferred embodiment, the MOI value in the preculture and the main culture is between $10^{-6}$ and 1.

In the method according to the invention, the main culture is usually carried out in a fermenter of a suitable size. In fermenters, the individual ambient parameters such as air infeed, pH, nutrient addition and the like can be controlled continuously. In a preferred embodiment, the growth of the main culture takes place with a reduced infeed of air and the pH is preferably also kept within a range of between 5.8 and 7.8.

After the fermentation, the bacteriophages are usually obtained from the fermentation broth by first centrifuging and/or filtering off the fermentation medium so that the cell constituents originating from the lysed bacteria are separated off. The supernatant liquid is preferably filtered through one or more filters in this case, the pore size being selected such that any bacteria which may still be present are unable to pass through the filters at the time of the first filtration. The pore size of these filters is preferably in a range of between 0.1 and 1.0 µm, preferably of between 0.1 µm and 0.5 µm, even more preferably of between 0.1 µm and 0.45 µm, and most preferably of between 0.1 and 0.2 µm. Because of their smaller size, the bacteriophages are able to pass through filters of this size. However, care must be taken to see that the filters used are ones on which, as far as possible, the bacteriophages do not adsorb because, if they did, this might lead to the filters becoming clogged and to a worsening of the yield of phages.

In a further step, the solution containing the phages is preferably diafiltered in such a way that the bacteriophages are unable to pass through the pores and are thus concentrated in the solution. The concentration of the bacteriophages can be readily determined by standard methods of microbiological determination. The solution preferably contains a concentration of at least $10^{10}$ PFU's (plaque-forming units) per ml.

Within the scope of the present invention, a mixture of at least two or more bacteriophages is used. A mixture of this kind is preferably so produced that a solution containing a defined concentration of phages is first produced from each phage to be used and these solutions are then mixed together in the desired ratio. The bacteriophages concerned may belong to the same phage classes or even to different phage classes. In an embodiment which is a particular preference, the mixture of bacteriophages consists of two different classes of Myoviridae. As a particular preference, the mixture of bacteriophages has on the one hand the bacteriophage of the KP3 type and/or the bacteriophage identified as MP13.3. As well as these, the mixture may also comprise other suitable bacteriophages.

Under the Budapest Treaty, two preferred bacteriophages were deposited at the German Collection of Microorganisms and Cell Cultures [Deutsche Sammlung von Mikroorganismen and Zellkulturen GmbH or "DMSZ"] located at Inhoffenstrasse 7B, 38124 Braunschweig (Brunswick), Germany, on 18 Oct. 2006. The bacteriophage strain MP13.3 was assigned the accession number DSM 18722 and the bacteriophage strain designated KP3 was assigned the accession number DSM 18723.

The mixture of bacteriophages is produced in such a way that each bacteriophage strain is first reproduced individually in the host bacteria. After each bacteriophage preparation has been purified and its titre determined, the mixture is then produced, in which case the ratio between the individual bacteriophages may vary over the range between 1:10 and 10:1. The mixture used is preferably one which consists of approximately equal proportions of the two bacteriophages, with the proportions of each of them being based on plaque-forming units. Further bacteriophage strains, which have been reproduced separately, may also be added to this mixture.

The phage mixture according to the invention may undergo suitable further treatment for use as a medicament. In these stages, care must be taken to see that the bacteriophages are not inactivated. The addition preferably takes place of protective substances such for example as thickening substances, e.g. glycerine or polyethylene glycol. Additives of this kind are preferable when medicaments are being administered in the form of liquids.

In a further preferred embodiment, the phage mixtures according to the invention have stabilisers, a particular preference being for human serum albumin.

In a preferred embodiment, the phage mixture according to the invention is used as a medicament in such a way that the bacteriophage solution has added to it at least one enzyme which has a synergistic effect on the efficiency of the bacteriophage solution. The enzymes in question may be ones which are themselves bactericidal. Use may thus be made of lysins, such as lysozyme for example, which originate from various sources, or in other words from bacteriophages, from bacteria (endolysins, exolysins) or from other sources. As an alternative to this, use may be made of lysozyme which may be isolated from, for example, chicken's eggs and which is able to lyse the bacterial cell wall, particularly of gram-positive bacteria. Other enzymes which may likewise be used with advantage belong to the group of proteases and/or peptidases. One example which may be given in this case is papain. Finally, the enzymes may also be nucleases or glucosaminidases which, although not themselves directly bactericidal, do assist the action of the bacteriophages.

In an embodiment which is a particular preference, the enzyme is the protease serralysin, which is produced from the strain *Serratia marcescens*. Another preferred enzyme is the nuclease benzonase or dornase α. In Example 7, the superior properties of this combination in a biological matrix (saliva) are disclosed.

If the mixture of bacteriophages according to the invention is to be applied in a different form, it may also be advantageous for the mixture to be lyophilised. In this case too suitable protective constituents such as various sugars may be added.

The medicaments according to the invention may be applied in the form of a solution, tincture, salve or lotion. In another preferred embodiment, a medicament of this kind also contains, as well as the mixture of phages, an antibiotic which is preferably effective against gram-positive bacteria. The background to this combination is the fact that methicillin-resistant bacteria are to be lysed by the phage mixture according to the invention. However, at the same time the intention is also to prevent any other bacteria which may be present and which are not resistant to antibiotics from being able to flourish again. Because antibiotic resistances are often coded on plasmids in *staphylococci*, bacteria which are, in themselves, antibiotic-sensitive might absorb the plasmids from the lysed bacteria. This is prevented by the preferred combination.

The phage mixture according to the invention is preferably used to produce a medicament which is used for the therapy of infections which are caused by antibiotic-resistant strains of *Staphylococcus aureus*. In a preferred embodiment, these infections are ones which occur on the skin or the mucous membranes. These infections can be easily and effectively treated by the mixtures of bacteriophages according to the invention. An advantage which exists in this case is that the mixture of bacteriophages does not have to be administered intravenously and/or intramuscularly but can simply be applied to the area infected in the form of a solution, powder, spray or salve.

The mixture of bacteriophages according to the invention can be used on the one hand for the therapy of an infection which already exists. However, under another aspect of the invention, the mixtures of bacteriophages can also be used to prevent the risk of an infection by antibiotic-resistant strains of *staphylococcus*. The mixture of bacteriophages is used prophylactically in this case. In an embodiment which is a very particular preference, the mixtures of bacteriophages of the present invention may be used both therapeutically and also prophylactically, in particular to either treat or avoid the risk of an infection of the lungs. The lungs are often subject to an increased risk of infection because bacteria, and particular antibiotic-resistant bacteria, are easily able to find their way into the lungs through breathing and ventilation equipment.

Another preferred field of application for the phage mixture according to the invention is application to the eyes. If there is an infection of this kind, the phage mixture is administered in the form of eye drops.

The method according to the invention is shown in schematic form in FIG. 1.

Figure 1:
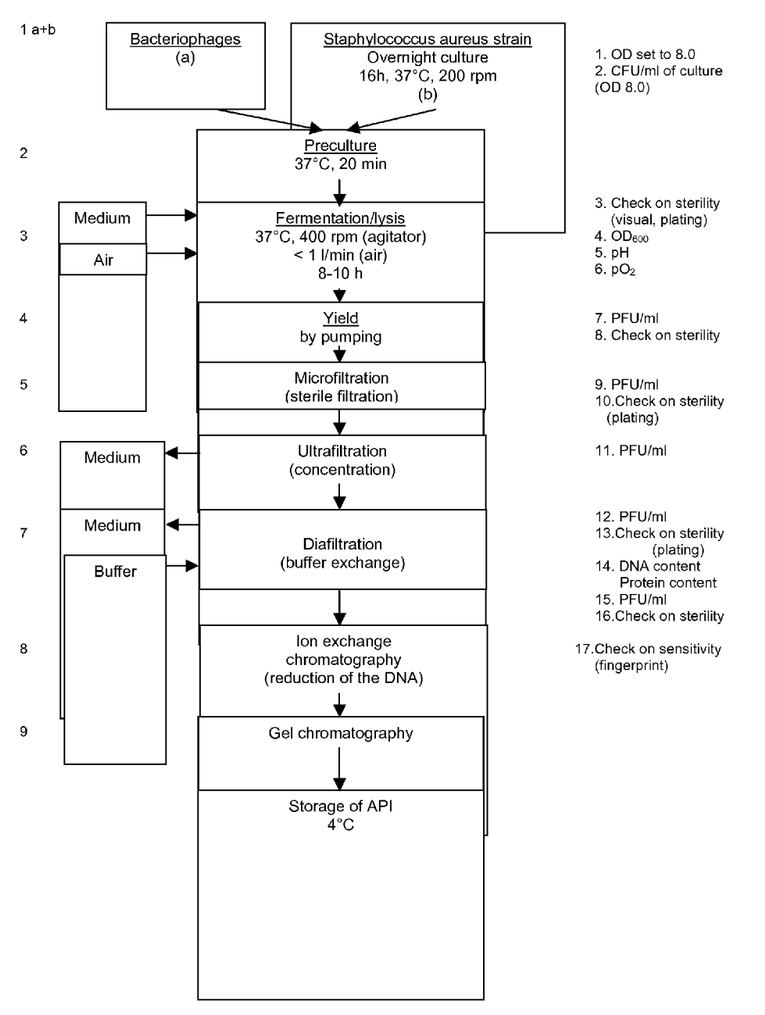

In a preferred embodiment of method according to the invention, benzonase is added to the solution containing bacteriophages. High-molecular-weight DNA which originates mainly from the lysed *staphylococci* is cleaved by the benzonase in such a way that there need be no fear of infectiousness or of possible recombination with fragments of the *staphylococcus* DNA. On the other hand, the benzonase has a beneficial effect on the bacteriophage solution in respect of its viscosity. The benzonase is therefore preferably added either before the microfiltration or after the diafiltration. If benzonase is added, it is advisable for gel chromatography also to be carried out after the purification by ion exchange chromatography. The remnants of the benzonase which are still present are separated off by this means. The molecular weight of benzonase is between 30,000 and 40,000 daltons. It is therefore advisable for the column material used for the gel chromatography to have a void volume for approximately 100,000 daltons, preferably one for approximately 50,000 daltons.

A significant further advantage of the addition of benzonase is that the yield is increased in the ion exchange chromatography. In other words, fewer bacteriophages are lost because there is a beneficial effect on the complexing with the nucleic acid in the sense that the yield is higher.

Another preferred aspect of the present invention is that the bacteriophage suspension can be stabilised by the addition of human serum albumin. This may be human serum albumin which is obtained from human plasma. However, any viral contaminants have to be removed in this case. As an alternative to this, use may also be made of human serum albumin produced by recombinant processes to avoid the risk of viral contamination.

In a further preferred embodiment, bacteriophage solution is stabilised by adding magnesium ions in a concentration which is between 0.1 and 100 mM, preferably between 1 and 10 mM, of $Mg^{2+}$. In an embodiment which is a very particular preference, the stabilisation is achieved by the addition of a combination of magnesium ions and human serum albumin.

The following examples are intended to explain the present invention.

EXAMPLE 1

Phage Production in a Fermenter 1.1 Micro-Organisms
Bacteria for Fermentation
    MRSA M.03.02.0028, a frozen culture of a strain which was obtained from Prof. Daschner of Freiburg. Under the Budapest Treaty, the strain has been deposited at the German Collection of Microorganisms and Cell Cultures under the number 18421.
Bacteria for Plaque Test
    *Staphylococcus aureus* M.03.02.0008, obtained from Prof. Daschner of Freiburg. Under the Budapest Treaty, the strain has been deposited at the German Collection of Microorganisms and Cell Cultures under the number DSM 18421.
Phages
    Starting phages I, sterile filtered
    Concentration: $1 \times 10^{10}$ PFU/ml
    The two bacteriophages strains KP3 (DSM 18723) and MP13.3 (DSM 18722) were each grown separately.
1.2 Nutrient Media
a) APS LB Broth
    20 g of ready-made medium (Becton Dickinson, batch no. 430510) was weighed out, dissolved in de-ionised water and topped up to a final volume of 1 l. The natural pH of the medium produced in this way was approx. 6.8 and did not need to be set. The medium was sterilised for 20 min at 121° C. and was then set aside at room temperature (RT; 20-22° C.).

b) APS LB broth (fermentation)

20 g of ready-made medium (see above)+2.5 g of $MgSO_4$ (Roth, pro analysi) were weighed out, dissolved in de-ionised water and topped up to a final volume of 1 l. The medium was sterilised for 20 min at 121° C. in a MediaPrep preparator and was then poured directly into the sterilised culture vessel.

c) LB medium 10 g of tryptone from casein (Roth, for microbiology), 5 g of NaCl (Roth, pro analysi) and yeast extract (Roth, for bacteriology) were dissolved in de-ionised water and topped up to a final volume of 1 l.

To produce solid nutrient medium, 15 g of agar agar/l (Roth, high purity) was added. The medium was sterilised for 20 min at 121° C. The agar plates were stored at room temperature. The plates used for the test were ones which had been stored under these conditions for a maximum of 1 week.

d) Vogel-Johnson Agar 58 g of ready-made medium (Merck) was dissolved in 1 l of hot, de-ionised water and was then sterilised for 20 min at 121° C. The medium was cooled to approx. 50° C. and 0.24 g/l of potassium tellurite (a sterile filtered solution) was then added. The medium was poured into Petri dishes, was dried for 30 min on a clean bench and was then kept at 4° C.

e) LB top agar 1.0 g of tryptone from casein,
0.5 g of NaCl,
0.8 g of agar agar, were dissolved in de-ionised water, and the mixture was topped up to 100 ml and was then sterilised for 20 min at 121° C. Until it was used, it was kept in a drying cabinet at 60° C.

1.3 Buffers a) 0.85% NaCl 0.85 g of NaCl was dissolved in de-ionised water and topped up to a final volume of 100 ml. The buffer was sterilised for 20 min at 121° C.

b) Phage Buffer 20 mM of tris (pH 7.4), (Roth, ultra quality),
100 mM of NaCl,
10 mM of $MgSO_4 \times 7H_2O$ Production took place from sterile stock solutions and sterile de-ionised water. Storage was at RT.

c) 1 M of NaOH 40.01 g of NaOH (Roth) was dissolved in de-ionised water and topped up to a final volume of 1 l. The solutions was sterilised for 20 min at 121° C. and then kept at RT.

d) pH Calibrating Solutions pH 4.01 (Mettler Toledo)
pH 7.00 (Mettler Toledo)

e) Oxygen probe ($pO_2$ Probe; Measures the Partial Pressure of Oxygen in a Medium)

To calibrate the $pO_2$ probe, the Calibration button was first clicked on the Task bar and then the $pO_2$ button was clicked in the next window. In this case too the temperature value was set to room temperature or the temperatures of the solutions were entered.

f) Optical Density Probe

The OD probe was not calibrated but simply reset to zero for the given medium at each new run. Because the probe had not as yet been linearised, there was no need for the external comparison with the $OD_{600}$ as measured by photometer.

g) Measurement of pH

The pH meter was switched on prior to the measurement and the temperature required was set. The pH meter was checked for its state of calibration and if necessary was calibrated following the manufacturer's instructions. The probe was removed from the 3 M of KCl solution and flushed clean with de-ionised water. The probe was dried with a paper towel and held in the solution to be measured. The measuring process could be speeded up by rocking or stirring the solution. A note was made of the value measured, the probe was taken out of the solution and flushed thoroughly with 70% ethanol and then with de-ionised water, was dried with a paper towel and was then put back in the 3 M of KCl solution to stand.

1.5 Growing of Bacterial Strain

Of the strain specified in 1.1, a frozen glycerine culture prepared for the fermentation was taken from a freezer cabinet at −80° C. and was thawed on a clean bench 2 inoculation loops of cell material were inoculated into 20 ml of APS LB medium and were incubated overnight at 37° C. and 200 rpm while being shaken.

1.6 Fermentation

The culture was taken from the shaker incubator operating at 37° C.

0.1 ml was extracted for the measurement of optical density, was diluted 1+9 with medium (0.9 ml of APS-LB+ 0.1 ml of culture) and a mean $OD_{600}$ value of 1.363 was measured.

A sample was taken of the medium with flexible withdrawal tubing and poured into an Eppi (=reaction vessel made by the Eppendorf company). 500 µl each was plated onto LB agar and Vogel-Johnson agar and was incubated overnight at 37° C.

1.7 Setting of the Overnight Culture to an OD of 8.0

The culture was mixed with medium in a sterile Falcon tube and was set to an optical density of approximately 8.0 by dilution with sterile medium.

1.8 Incubation of Bacteria/Phages

The phages to be used (1.1) were diluted to $2 \times 10^{-2}$ in phage buffer in Eppi's (final volume=2 ml of the $2 \times 10^{-2}$ dilution)

When the temperature in the vessel was steady, 15 ml of set bacterial culture and 2 ml of phages were mixed in a Falcon tube and were incubated for 20 min at 37° C.

The mixture of bacteria and phages was drawn into a 20 ml syringe through a needle and was injected via the septum in the cover of the culture vessel.

After 3 min of agitation, the first measured values were determined for the fermentation.

1.9 Determination of CFU/ml

The culture was set to an OD of 8.0 and a factor-of-ten dilution series thereof was pipetted to the specification given below

TABLE 1

| $10^{-1}$ | $10^{-2}$ | $10^{-3}$ | $10^{-4}$ | $10^{-5}$ | $10^{-6}$ | $10^{-7}$ | $10^{-8}$ |
|---|---|---|---|---|---|---|---|
| 450 µl of 0.85% NaCl + 50 µl of culture | 450 µl of 0.85% NaCl + 50 µl of $10^{-1}$ | 450 µl of 0.85% NaCl + 50 µl of $10^{-2}$ | 450 µl of 0.85% NaCl + 50 µl of $10^{-3}$ | 450 µl of 0.85% NaCl + 50 µl of $10^{-4}$ | 450 µl of 0.85% NaCl + 50 µl of $10^{-5}$ | 450 µl of 0.85% NaCl + 50 µl of $10^{-6}$ | 450 µl of 0.85% NaCl + 50 µl of $10^{-7}$ |

2×100 µl of the $10^{-6}$-$10^{-8}$ dilutions were plated onto LB agar (with a Drigalski spatula)

The plates were incubated overnight at 37° C. the next day.

1.10 Fermentation

Once the fermentation had started, the parameters were read off or measured, as the case may be, every 30-60 min.

The measurements of $OD_{600}$ were made against the fermentation medium as a blank value The sampling (8 ml at a time) during the fermentation was performed via flexible withdrawal tubing using a sterile 10 ml syringe each time.

Of the 8 ml, 1 ml was used for the $OD_{600\ external}$ measurement (either placed directly in a cuvette or poured into an Eppi) and the rest was used for the $pH_{external}$ measurement.

MOI: 1/130 (phages/bacteria)=0.0077

On this occasion too, the lysis began after a little less than 3 hours. This appears to be the period which can be expected for the beginning of the lysis because it occurred at the same point in time when the fermentation was repeated. The fermentation process appears to be highly repeatable because each time the partial pressure of oxygen had dropped to 0.0% after 2 h 15 min and was again >0.0% 30 min later. The OD as measured after given intervals of time over the process was also almost identical. The bacteria each time reached an OD of 1.5 as their highest value. When the fermentation was stopped after 7 h 15 min, an $OD_{600}$ of 0.179 (A12: $OD_{600}$ 0.22) was still measurable. However, the large number of viable *staphylococci* in the product of fermentation on the Vogel-Johnson agar (see section 5.1.2) indicated that the fermentation/lysis was not yet absolutely complete.

TABLE 2

Values obtained for the fermentation

| Time | Temp. °C. | $pO_2$ % | pH internal 37° C. | pH external RT | OD internal CU* | OD external 600 nm Dilut. | Air infeed l/min | Agitator rpm |
|---|---|---|---|---|---|---|---|---|
| 9:05 before | 34.6 | 96.1 | 6.45 recal. 6.71 | 6.71 | 0.020 | x | x | <1 | 396 |
| 09:05 before inject. | 37 | 101.1 | 6.71 | x | 0.022 | x | x | <1 | 396 |
| 10:00 start | 37 | 95.1 | 6.69 | 6.71 | 0.045 | — | 0.066 0.060 | <1 | 396 |
| 11:00 | 37 | 78.8 | 6.62 | 6.65 | 0.120 | — | 0.211 0.212 | <1 | 396 |
| 12:05 | 37 | 4.6 | 6.22 | 6.25 | 0.390 | 1 + 1 | 0.516 0.515 | <1 | 396 |
| 12:15 | 37 | 0.0 | 6.15 | x | 0.410 | x | x | <1 | 396 |
| 12:50 | 37 | 20.1 | 5.91 | 5.99 | 0.520 | 1 + 4 | 0.282 0.278 | <1 | 396 |
| 13:50 | 37 | 91.1 | 5.98 | 6.04 | 0.330 | 1 + 1 | 0.283 0.279 | <1 | 396 |
| 14:50 | 37 | 99.0 | 6.05 | 6.08 | 0.220 | — | 0.316 0.314 | <1 | 396 |
| 15:50 | 37 | 100.4 | 6.08 | 6.12 | 0.190 | — | 0.230 0.230 | <1 | 396 |
| 16:50 | 37 | 101.0 | 6.10 | 6.14 | 0.190 | — | 0.189 0.184 | <1 | 396 |
| 17:50 | 37 | 101.3 | 6.11 | 6.14 | 0.180 | — | 0.179 0.176 | <1 | 396 |

*Because of the turbulence due to the agitation at 400 rpm, the values fluctuated to and fro and the value shown in this column is thus only able to indicate a trend.
x = No measurement made
recal. = Values recalibrated (called up by clicking "Calibration" on the fermenter interface and then "Recalibration", and then entering the value)

1.11 Results

The overnight culture used was one which, after adjustment of the OD to 8.0, showed a concentration of $8.5 \times 10^8$ CFU/ml (CFU=colony forming units).

Calculation of MOI Value:
Bacteria: 15 ml×$8.5 \times 10^8$ CFU=$1.3 \times 10^{10}$ bacteria per ml
Phages: 2 ml×$5 \times 10^7$ PFU/ml (given by $2 \times 10^{-2}$ dilution)= $1 \times 10^8$ PFU (plaque forming units per ml)

The phage concentration of $5.4 \times 10^9$ PFU/ml found in the fermentation was between the values which were obtained for other fermentations ($3.3 \times 10^9$ PFU/ml and $8.3 \times 10^9$ PFU/ml). A yield of $5 \times 10^9$ PFU/ml was also obtained in a shake flask, which means that this was a perfectly satisfactory result. If the lysis continues to progress at 4° C., a higher yield can be achieved.

EXAMPLE 2

Production of a Mixture of Bacteriophages

The production strain, a strain of methicillin-sensitive *Staphylococcus aureus* which has been deposited at the German Collection of Microorganisms and Cell Cultures under the number 18421, was first cultivated overnight in approximately 250 ml of nutrient medium at a temperature of 30° C. By diluting it with fresh sterile medium, the bacterial culture which was grown was set to an optical density of approximately 1.0. The diluted bacterial culture was then mixed with a suitable quantity of the bacteriophages in such a way as to set a ratio of phages to bacteria of approximately 1. The mixture of bacteria and bacteriophages was then pre-incubated for approximately 5 hours at a temperature of 30° C.

After 5 hours of pre-incubation, the bacteria/bacteriophage mixture was transferred to a 10 liter fermenter in which the above-mentioned strain of methicillin-sensitive *Staphylococcus aureus* had been fermented to an optical density of 2.0 at 37° C. Having been mixed with the pre-culture, the pre-fermented bacteria were fermented for a further 12 hours at 37° C. The fermentation was then stopped and the fermentation broth containing bacteria, remnants of bacteria and phages was first pre-purified by deep filtration. In the deep filtration, the fermentation broth was filtered through a filter element which was of a pore size which readily allowed the bacteriophages to pass through. Because bacteriophages often have negative charges, the filter element had negative charges to prevent any unwanted adsorption of the bacteriophages on the filter element.

After the deep filtration, the fermentation broth was filtered through a filter of a pore size diameter of approximately 0.1 to 1 µm to remove bacteria and bacterial constituents, in particular membrane constituents.

Since the solution containing the bacteriophages which was obtained after the microfiltration was very large in volume, the volume was considerably reduced by ultrafiltration. In the ultrafiltration, the pore size of the filter was selected to be such that only the solvent of the fermentation broth, i.e. water, and components of the nutrient medium dissolved therein were removed by the filtering. This greatly increased the concentration of the bacteriophages, and what is usually achieved is concentration of the bacteriophages by a factor of between 100 and 10,000.

The concentrated mixture of bacteriophages was then mixed with benzonase, which removed the remaining bacterial nucleic acids. The bacteriophage solution was then adsorbed on an ion exchanger and was then eluted with a salt gradient. The fractions which contained the bacteriophages were then further purified by gel chromatography and the bacteriophage solution obtained in this way was set to have the desired concentration of bacteriophages. To produce the mixture, the two bacteriophages which are preferred in accordance with the invention were grown separately and purified and then mixed.

The mixture of bacteriophages was then converted to a desired form, i.e. a solution, salve, powder or granular material capable of application, and placed in a container and could then be used.

EXAMPLE 3

Stability of the Bacteriophage Preparation at 4° C., Room Temperature and 37° C.

A phage buffer of the following composition was used as a buffer for storage: 20 mM of tris (pH 7.4), 100 mM of NaCl, 10 mM of $MgSO_4 \times 7H_2O$. Production was from sterile stock solutions and sterile de-ionised water. Human serum albumin (HAS) at a concentration of 1 g/l was used as a stabiliser. This product was purchased from Baxter.

The two bacteriophages MP13.3 and KP3 were examined.

To determine the PFU, *Staphylococcus aureus*, as deposited at the German Collection of Microorganisms and Cell Cultures under the number 18421, was grown in LB medium. Using the overnight culture, a 100 ml conical flask containing 20 ml of LB medium was inoculated in such a way as to give an $OD_{600}$ of 0.2. The culture was then incubated in a shaker incubator at 37° C. and 200 rpm until such time as an $OD_{600}$ of between 0.8 and 1 was obtained.

From the phage solution to be examined, a factor-of-ten dilution series in phage buffer was prepared (100 µl of phage+ 900 µl of phage buffer).

Of the diluted phages, twin 100 µl samples of each were pipetted with a sterile filter syringe into the bottoms of sterile, labelled centrifuge tubes. 100 µl of phage buffer was placed in a tube as a control. 100 µl of DSM 18421 ($OD_{600}$ of 0.8 to 1.0) was then mixed into all the tubes. The tubes were sealed with aluminium caps, carefully shaken and pre-incubated for 20 min at 37° C. together with the associated agar plates in an incubator.

Approximately 2 min before the end of the pre-incubation, LB top agar was taken from a cabinet heated to 60° C. and mixed in a magnetic stirrer for 1-2 min at room temperature. The warmed plates, the tubes and the top agar were placed on a clean bench after the incubation.

6 ml of the top agar was drawn up in a 5 ml pipette (accurately scaled beyond the 5 ml level) and 3 ml was distributed into each of two centrifuge tubes. The tubes were mixed for 2 seconds on a vortexer and were then poured smartly onto the associated agar plates and spread. The agar plates were dried on a clean bench for at least 10 min before being transferred to the incubator, which was at 37° C., and were incubated overnight upside-down.

TABLE 3

Stability of MP4 with and without HSA

| Days | HSA | 0 | 1 | 7 | 14 |
|---|---|---|---|---|---|
| 4° C. | Without | 3.10E+09 | 3.00E+09 | 2.20E+09 | 1.70E+09 |
|  | 1 mg/ml | 3.10E+09 | 2.70E+09 | 2.70E+09 | 2.30E+09 |
| RT | Without | 3.10E+09 | 2.90E+09 | 2.10E+09 | 1.40E+09 |
|  | 1 mg/ml | 3.10E+09 | 2.70E+09 | 2.70E+09 | 2.40E+09 |
| 37° C. | Without | 3.10E+09 | 1.30E+09 | 6.40E+07 | 1.20E+06 |
|  | 1 mg/ml | 3.10E+09 | 2.30E+09 | 1.50E+09 | 6.50E+08 |

Values are in PFU/ml

Table 3 shows the results of the stabilisation which was achieved by the addition of human serum albumin, taking the MP13.3 bacteriophage as an example. The notation used in Table 3 is a different way of representing the phage concentration. Thus, 3.10 E+0.9 for example means $3.10 \cdot 10^9$ PFU of phages per ml of solution.

Long-term stability too was examined, taking MP4 as an example, measurements being made of the preparations at 4° C. for a period of up to 32 weeks. The results are shown in Table 4. The abbreviation M phage (MP) stands for the MP13.3 bacteriophage (DSM 18722) and the abbreviation K phage stands for the KP3 bacteriophage (DSM 18723).

TABLE 4

| 4° C. | Day 0 | Day 1 | Week 1 | Week 2 | Week 3 | Week 8 |
|---|---|---|---|---|---|---|
| M phage | 1.01E+10 | 9.53E+09 | 7.68E+09 | 9.77E+09 | 9.09E+09 | 1.06E+10 |
| K phage | 1.13E+10 | 8.63E+09 | 6.70E+09 | 8.32E+09 | 9.76E+09 | 9.94E+09 |
| M phage + K phage | 2.07E+10 | 1.65E+10 | 1.77E+10 | 1.54E+10 | 2.04E+10 | 2.00E+10 |

| 4° C. | Week 12 | Week 18 | Week 25 | Week 28 | Week 32 |
|---|---|---|---|---|---|
| M phage | 18.40E+09 | 8.41E+09 | 1.09E+10 | 9.51E+09 | 8.55E+09 |
| K phage | 7.96E+09 | 8.11E+09 | 1.10E+10 | 9.33E+09 | 9.08E+09 |
| M phage + K phage | 1.90E+10 | 1.64E+10 | 2.20E+10 | 1.98E+10 | 1.75E+10 |

Storage at 4° C. with 1 mg/ml of HSA (Baxter)
Values are in PFU/ml

EXAMPLE 4

Determination of Specific Activity a) Determination of Protein Concentration In an acid medium, Coomassie Blue G-250 forms, with protein, a blue colour complex which can be quantified photometrically at $\lambda=595$ nm with the help of a microtitre reader (96 wells per microtitre plate, 300 µl per well).
Materials:
Coomassie® Protein Assay Reagent (ready-made solution) from Pierce (product number: 23200)
Standards (500 µl aliquots at 1 mg/ml)
  γGlobulin (e.g. BioRad, catalogue number: 500-0005)
  Bovine serum albumin (BSA) (e.g. BioRad, catalogue number: 500-0007)
Procedure:

An aliquot of the suitably diluted sample was added to the reagent and measured photometrically over a defined interval of time. The total protein concentration in mg/l or µg/l was calculated from the standard curve with due allowance for the dilution factor.
b) Phage Activity
Principle of Testing:

Quantitative determination of the infectiousness/activity of a phage suspension is performed by means of a plaque assay. The principle on which the assay is based is the lytic effect specific to *Staphylococcus aureus* which the phages used have. The reproduction of the phages in a carpet of host cells produces clear centres of activity, so-called plaques, which are visible on the macroscopic scale and which stand out clearly from their surroundings.

Given a suitable MOI (multiplicity of injection), precisely one plaque can be attributed to the infection of a bacterial cell by a single infectious phage. The phage activity in PFU (plaque forming units)/ml can be calculated from the volume of the sample used, the dilution of the sample and the number of plaques found per plate.

If the phage titre of the sample to be measured is known, the dilution and the volume of the sample are selected such that the number of plaques per agar plate is between 50 and 250. If the exact phage titre of the sample is not known, a quite wide spectrum has to be covered by way of the volume of the sample or the graduations of dilution.
Materials:
*Staphylococcus aureus* DSM 18421
Procedure:

The *Staphylococcus aureus* was grown in a shaken culture in two stages.

An aliquot of the sample was incubated for a short period with an aliquot of the *staphylococcus* culture.

The suspension was mixed with liquid agar and the agar was plated onto a prepared agar assay plate.

The agar assay plate was incubated for 18-22 h.

The plaques were counted.

The activity was calculated in PFU/ml.
c) Specific Activity

Specific activity is defined as the ratio of the activity to the protein, in PFU/µg of protein. The values measured were as follows:

TABLE 5

|  | Total protein (µg/ml) | Activity (PFU/ml) | Specific activity (PFU/µg of protein) |
|---|---|---|---|
| K phage | 25.5 | 2.42E+10 | 0.09E+10 |
| M phage | 26.5 | 6.48E+10 | 0.24E+10 |

In the solution which is used, the phages which are used in accordance with the invention preferably have a specific activity of at least $10^8$ PFU/µg of protein and, as a particular preference, a specific activity of $9 \cdot 10^8$ (corresponds to 0.09 E+10) in the case of the K phages and of $2.4 \cdot 10^9$ (0.24 E+10) in the case of the M phages (each in PFU/µg of protein). The following values were found for different batches:

TABLE 6

| Batch designation | Total protein (µg/ml) | Activity (PFU/ml) | Specific activity (PFU/µg of protein) |
|---|---|---|---|
| SA1-ABT-031 (M phage) | 27 | 6.48E+10 | 0.24E+10 |
| SA1-ABT-032 (M phage) | 26 | 5.07E+10 | 0.20E+10 |
| SA1-ABT-034 (K phage) | 26 | 5.19E+10 | 0.20E+10 |
| SA1-ABT-035 (K phage) | 27 | 2.42E+10 | 0.09E+10 |

EXAMPLE 5

Use of Benzonase

Benzonase is an endonuclease which is highly efficient at breaking down DNA and also RNA into extremely small units. This enzyme is used principally for reducing viscosity.

Another principal field of use is the prevention of interactions between DNA and large proteins. These interactions may make efficient purification more difficult or may even prevent it completely. This would particularly affect the present process, where allowance has to be made for the very large protein membrane of the phage. The method according to the invention was carried out once without treatment with benzonase and once with treatment with benzonase. The results are shown in Tables 7 and 8

TABLE 7

Ion exchange chromatography without benzonase

| Fraction | Bacteriophages Total PFU | Recovery % | O.D. 260/280 | Protein µg | Spec. activity PFU/µg |
|---|---|---|---|---|---|
| At start | $16 * 10^{10}$ | | 1.72 | 545.7 | $0.029 * 10^{10}$ |
| Peak 1 | $4.2 * 10^{10}$ | 26 | 1.28 | 31 | $0.135 * 10^{10}$ |
| Peak 2 | $0.9 * 10^{10}$ | 6 | 1.79 | 16 | $0.056 * 10^{10}$ |
| | 17.6% lost | 32 | | | |

TABLE 8

Ion exchange chromatography with benzonase

| Fraction | Bacteriophages Total PFU | Recovery % | O.D. 260/280 | Protein µg | Spec. activity PFU/µg |
|---|---|---|---|---|---|
| At start | $114 * 10^{10}$ | | 1.72 | 785.7 | $0.145 * 10^{10}$ |
| Peak 1 | $49.1 * 10^{10}$ | 43 | 1.33 | 199.5 | $0.25 * 10^{10}$ |
| Peak 2 | $0.6 * 10^{10}$ | 1 | 1.96 | 60 | $0.01 * 10^{10}$ |
| | 1.2% lost | 44 | | | |

EXAMPLE 6

Effectiveness of the Mixture

To show that the mixture of bacteriophages according to the invention has surprising properties, various problem pathogens from a hospital were tested. The strains of *Staphylococcus aureus* showing multiple antibiotic resistance which were used were isolates which had been supplied by a hospital.

It was checked whether the various *Staphylococcus aureus* isolates could be lysed once by the MP13.4 phage, once by the KP4 phage and once by a 1:1 mixture of MP13.4 and KP4.

Table 9 below shows that by using a phage mixture it was possible to lyse even *Staphylococcus aureus* strains which could not be lysed by a single bacteriophage. Because, when multiple-antibiotic-resistant strains of *Staphylococcus* are being treated in hospital, these pathogens have to be lysed as quickly and effectively as possible, it is an inestimable advantage for a mixture of bacteriophages to be able to lyse, and thus destroy, as many different problem germs as possible.

TABLE 9

Comparison of the effectiveness of the bacteriophages against resistant strains of *staphylococcus aureus* both individually and as a mixture

| No. | Strain* | MP13.4 $1 \times 10^8$ (PFU/ml) | KP4 $1 \times 10^8$ (PFU/ml) | Mix of MP13.4 + KP4 1:1 $1 \times 10^8$ (PFU/ml) |
|---|---|---|---|---|
| 1 | MRSA 0151 | 0 | +++ | +++ |
| 2 | MRSA 0166 | +++ | +++ | +++ |
| 3 | MRSA 0226 | +(+) | + | +(+) |
| 4 | MRSA 0232 | +++ | (+) | +++ |
| 5 | MRSA 0486 | +++ | +++ | +++ |
| 6 | MRSA 0703 | +++ | (+) | +++ |
| 7 | MRSA 0975 | 0 | +++ | +++ |
| 8 | MRSA 1188 | +++ | (+) | +++ |
| 9 | MRSA 0811 | +++ | +++ | +++ |
| 10 | MRSA 1204 | +++ | + | +++ |
| 11 | *S. aureus* 12535-2 | +++ | 0 | +++ |

*The strains were problematic isolates from a hospital which were resistant to a large number of antibiotics.
0 = no lysis; + = weak lysis; ++ = better lysis and +++ = very good lysis.

EXAMPLE 7

Lysis of *Staphylococcus aureus* DSM 18421 in Saliva 7.1 Production of a Mixture of Saliva
  Morning saliva (before breakfast and before cleaning of teeth) was collected from different individual persons.
  The saliva samples were centrifuged for 5 min at room temperature at 12,000 rpm.
  The supernatant liquid was removed and sterile filtered (0.8 µm pre-filter, then a 0.22 µm filter).
  The samples of saliva were mixed 1:1 in a sterile vessel.
7.2 Incubation of the Preparations for Lysis
  To the saliva prepared as described above were also added:
    approx. $1 \times 10^4$ CFU/ml of DSM 18421 (from a suitable dilution of the overnight culture),
    approx. $1 \times 10^8$ PFU/ml of phages (Simba Top, 1:1 mixture of purified M and K phages).
  Used in addition were serralysin (100 U/ml), dornase (25 µml) or benzonase (25 µml) or a combination of these enzymes.
  The enzymes were added right at the start of the incubation.
  A control incubation was carried out at the same time in which the phages were replaced by adding the same volume of storage buffers (for composition see below).
  The total volume of all the preparations was 2 ml.
  The incubation was carried out in 10 ml glass penicillin bottles at 37° C. and 200 rpm (in a shaker incubator)
7.3 Determination of the Viable Cell Count (CFU/ml) After 6 h
  After an incubation period of 6 h, an aliquot was taken from each preparation and a factor-of-ten dilution series prepared from it.
  2-5 suitable dilutions were selected from each dilution series and $2 \times 100$ µl (twin samples) of each were plated (with a Drigalski spatula).
  The plating was performed onto LB agar in the case of the phage-free preparations and onto LB agar containing 0.01% citrate in the case of the preparations containing phages.

After at least 16 h of incubation at 37° C., the colony forming units (CFU's) were counted on each plate Only plates which had at least 20 CFU's were used to calculate the FIGURE for CFU/ml A representation in graph form was prepared by plotting CFU/ml (in logarithmic form) against the period of incubation.

The results are shown in Tables 10 to 12.

TABLE 10

Serralysin with and without phages

| Preparation | CFU/ml | % |
|---|---|---|
| Control without phages | $8.80 \times 10^5$ | 100 |
| Control without phages + serralysin | $1.14 \times 10^6$ | 130 |
| +phages | $5.93 \times 10^5$ | 67.4 |
| +phages + serralysin | $1.65 \times 10^5$ | 18.7 |

Table 10 (serralysin with and without bacteriophages) takes an example to define the effect which serralysin has on the concentration of *S. aureus* in saliva when alone and when combined with bacteriophages (mixture of DSM 18722 and DSM 18723). As the Table shows, serralysin alone did not cause a reduction in the colony count. The mixture of bacteriophages produced a reduction in the colony count to 67.4%. When the bacteriophages and serralysin were combined, the colony count dropped to 18.7%. There was thus a synergistic effect.

TABLE 11

Comparison of dornase α and benzonase

| Preparation | CFU/ml | % |
|---|---|---|
| Control without phages | $3.31 \times 10^5$ | 100 |
| Control + phages | $6.20 \times 10^4$ | 18.7 |
| +phages + dornase α | $2.94 \times 10^4$ | 8.88 |
| +phages + benzonase | $2.11 \times 10^4$ | 6.37 |

Table 11 (comparison of dornase α and benzonase) takes an example to define the effect which the nucleases dornase α and benzonase have on the concentration of *S. aureus* in saliva. The use of bacteriophages caused a reduction in the colony count to 18.7%. A combination of bacteriophages and a nuclease reduced the colony count to 8.88% in the case of dornase α and to 6.37% in the case of benzonase.

TABLE 12

Comparison covering a combination of dornase α and serralysin with individual enzymes

| Preparation | CFU/ml | % |
|---|---|---|
| Control without phages | $4.97 \times 10^6$ | 100 |
| Control + phages + dornase α | $2.70 \times 10^6$ | 54.3 |
| +phages + serralysin | $1.40 \times 10^6$ | 28.2 |
| +phages + dornase + serralysin | $9.95 \times 10^5$ | 20.0 |

Period of incubation: 6 hours
Medium: saliva (human; mixture)

Table 12 (Comparison covering a combination of dornase α and serralysin with individual enzymes) takes an example to make a comparison of the effect which the nuclease dornase α and the proteinase serralysin have, individually and in combination, on the synergistic effect with bacteriophages. On their own, the enzymes reduced the colony count for *S. aureus* in saliva to 54.3% (dornase α) and 28.2% (serralysin). The two enzymes in combination caused a further reduction in the colony count to 20.0%.

EXAMPLE 8

Evidence of the Effect of a Combination of the Bacteriophages DSM 18722 and DSM 18723 on a Lethal *Staphylococcus aureus* Infection of the Lung in the Immunosuppressed Mouse Comparison with the use of antibiotics and comparison of different points of application for the bacteriophages The in vivo effectiveness of a mixture of the bacteriophages DSM 18722 and DSM 18723 was shown on an animal model (immunosuppressed mouse, intratracheal application of a virulent strain of *S. aureus*). A non-sensitive antibiotic (ciprofloxacin) and a sensitive antibiotic (vancomycin) were also used to allow a comparison to be made.

Four groups, each of 20 mice weighing approximately 25 g, were first subjected to immunosuppression to ensure that they would be adequately infected by *S. aureus*. The immunosuppression began with an application of cyclophosphamide 4 days before the bacterial infection. A further application of cyclophosphamide was carried out 1 day before, together with a once-only administration of cortisone. The immunosuppression with cyclophosphamide was repeated at intervals of 3 days.

Because existing pathogenic germs may possibly have an unwanted effect which proves lethal in mice if they are immunosuppressed (as was found to be the case in preliminary tests), the animals were protected for the period of the test with the antibiotic ciprofloxacin. The strain of *S. aureus* which was selected for the infection was resistant to this antibiotic.

The strain of *S. aureus* which was selected for the infection (internal designation M.06.02.0071) was an isolate which was supplied by the Robert-Koch-Institut of Wernigerode. This *S. aureus* is a member of the group of USA300 (MRSA, ST8) strains which are considered particularly virulent due to the presence of the virulence factor PVL. The strain selected was resistant to, amongst others, ciprofloxacin but was sensitive to vancomycin and clindamycin and certain other antibiotics.

On day 0, the mice had $1.5 \times 10^7$ CFU of the *S. aureus* applied to them intratrachially under anaesthetic.

The medicament, which was applied intratrachially under anaesthetic, was a one-off dose of $5.5 \times 10^{10}$ PFU of a 1:1 mixture of the bacteriophages DSM 18722 and DSM 18723 either one hour before the infection or one hour after the infection. One group, beginning 1 day before the infection, was also treated subcutaneously with vancomycin twice a day.

The main parameter was the determination of lethality as a function of the time elapsed since the start of the test. The length of the test was 14 days.

The results of the test are shown in Table 13:

TABLE 13

Percentage of surviving animals

| Hours after infection | 0 | 5 | 19 | 23 | 29 | 43 | 47 |
|---|---|---|---|---|---|---|---|
| Ciprofloxacin 2 × day + phages 1 × before infection | 100 | 100 | 100 | 90 | 70 | 50 | 50 |

TABLE 13-continued

| | Percentage of surviving animals | | | | | | |
|---|---|---|---|---|---|---|---|
| Hours after infection | 0 | 5 | 19 | 23 | 29 | 43 | 47 |
| Ciprofloxacin 2 × day + phages 1 × after infection | 100 | 100 | 90 | 75 | 60 | 25 | 25 |
| Ciprofloxacin 2 × day + vancomycin 2 × day | 100 | 100 | 100 | 95 | 70 | 45 | 40 |
| Ciprofloxacin alone 2 × day | 100 | 100 | 60 | 45 | 35 | 10 | 10 |

The bacteriophages can be seen to have a clear effect on lethality. In particular, the administration of the bacteriophages before the infection resulted in a considerable reduction in mortality in the acute phase. The effect which the application of the bacteriophages after infection had can also be seen. Similarly, a reduction in mortality compared with the placebo was also achieved in the acute phase by the prior and thereafter continuous administration of the antibiotic vancomycin, although it was rather less than in the case of the one-off administration of the bacteriophages before the infection.

The protective effect of the one-off administration of the bacteriophages before the infection was appreciably more pronounced at the end of the test (after 14 days) than was that of the protective and continuous administration of the antibiotic vancomycin.

The effect of the bacteriophages as an option for the treatment of *S. aureus* infections can be seen particularly clear as compared with the protective and then continuous administration of the antibiotic ciprofloxacin.

EXAMPLE 9

Nanocalorimetric Measurements

Another sensitive method of examining the activity of micro-organisms is available in the form of nanocalorimetry. In this technique, metabolic action is measured by way of the heat it produces. The production of heat is measured from the voltage (in [pV]) generated at thermocouples. Activators and inhibitors of metabolic action affect the production of heat and hence the voltage at the thermocouples.

A detailed description of the measuring system used and the procedure can be found in: J. Lerchner et al., Thermochimica Acta 477, 2008, 48-53.

The following nanocalorimetric investigations were carried out as part of the examination of the effectiveness of bacteriophages.
 Effect of a 1:1 mixture of the bacteriophages DSM 18722 and DSM 18723 on the metabolism of *S. aureus* DSM 18421
 Effect of the antibiotics vancomycin and clindamycin on the metabolism of *S. aureus* DSM 18421
 Effect of a 1:1 mixture of the bacteriophages DSM 18722 and DSM 18723 on the metabolism of *S. aureus* M.06.02.0071
 Effect of the antibiotics vancomycin and clindamycin on the metabolism of *S. aureus* M.06.02.0071
 Effect of a 1:1 mixture of the bacteriophages DSM 18722 and DSM 18723 and of the antibiotics vancomycin and clindamycin on the metabolism of *S. aureus* DSM 18421, after they have been used in the mouse pneumonia model and isolated from lung tissue.

Both the DSM 18421 strain of *S. aureus* and the M.06.02.0071 strain thereof are sensitive to the individual bacteriophages DSM 18722 and DSM 18723 and to the antibiotics vancomycin and clindamycin.

To carry out the investigations, vancomycin and clindamycin were used, each in a concentration of 10 μg/ml (corresponding to more than ten times the MIC which had been found in preliminary tests). The concentration of the bacteriophages was $4 \times 10^9$ PFU/ml.

The results of the measurements are shown in Tables 14-16. It can be seen from them that in the case of the bacteria the antibiotics produced a residual activity which can be interpreted as an indication of a stasis. After dropping below the minimum inhibiting concentration (MIC), the bacteria grew again. This causes a risk of resistance being developed or of treatment being inadequate.

The effect of the bacteriophages on the other hand results in practice in an irreversible inactivation, due to the lysis of the bacterium, and thus rules out the possibility of any renewed growth. The small remaining amount of heat production was attributable to enzymatic processes which were responsible for the breakdown of the biological material.

The nanocalorimetric measurements showed that the effect of the bacteriophages was superior to that of the antibiotics used.

TABLE 14

*S. aureus* DSM 18421

| Sample | Difference voltage [μV] | % relative to control |
|---|---|---|
| Baseline value | 0.059 | 0 |
| Control | −10.379 | 100 |
| Vancomycin | −3.681 | 36 |
| Clindamycin | −3.808 | 37 |
| DSM 18722 DSM 18723 1:1 | −1.497 | 15 |

TABLE 15

*S. aureus* M.06.02.0071

| Sample | Difference voltage [μV] | % relative to control |
|---|---|---|
| Baseline value | −0.145 | 0 |
| Control | −9.900 | 100 |
| Vancomycin | −4.132 | 41 |
| Clindamycin | −3.499 | 34 |
| DSM 18722 DSM 18723 1:1 | −3.287 | 32 |

TABLE 16

*S. aureus* from tissue (M.06.02.0071, mouse pneumonia model)

| Sample | Difference voltage [μV] | % relative to control |
|---|---|---|
| Baseline value | 0.386 | 0 |
| Control | −0.957 | 100 |
| Vancomycin | −0.438 | 61 |
| Clindamycin | −0.706 | 81 |

TABLE 16-continued

S. aureus from tissue (M.06.02.0071, mouse pneumonia model)

| Sample | Difference voltage [μV] | % relative to control |
|---|---|---|
| DSM 18722 DSM 18723 1:1 | −0.154 | 17 |

The invention claimed is:

1. A method for producing a mixture of bacteriophages comprising the steps of:
 a. growing a preculture of a methicillin-sensitive strain of Staphylococcus aureus species of bacteria;
 b. introducing at least two different separately reproduced strains of bacteriophage into the preculture of step (a), wherein said at least two different separately reproduced bacteriophage strains comprise at least two different serotypes of bacteriophage that specifically lyse bacteria of the species Staphylococcus;
 c. adding the preculture of step (b) to a main culture of a staphylococcus strain of bacteria at the time when the bacterial cells in the preculture begin to be lysed by bacteriophage to yield a combined culture of bacteria and bacteriophages; and
 d. purifying a mixture of bacteriophages from the combined culture of step (c), wherein the at least two different separately reproduced strains of bacteriophage set forth in step (b) and the mixture of bacteriophages set forth in step (d) comprise the bacteriophage MP13.3 having the accession number DSM 18722 and the bacteriophage KP3 having the accession number DSM 18723.

2. The method according to claim 1, characterised in that the methicillin-sensitive strain of Staphylococcus aureus has the accession number DSM 18421.

3. The method according to claim 1, wherein the combined culture of step (c) has a phage to bacteria ratio characterised by a multiplicity of infection (MOI) value between 0.01 and 1.

4. The method according to claim 1, wherein purifying step (d) comprises ion exchange chromatography and/or treatment with benzonase.

5. A phage mixture obtained by the method of claim 1, characterised in that the phages have a specific activity of at least $10^8$ plaque-forming units per μg of protein.

6. The phage mixture according to claim 5, characterised in that the mixture contains the bacteriophage MP13.3 (DSM 18722) and/or the bacteriophage KP3 (DSM 18723), each having a specific activity of at least $10^8$ PFU/μg of protein.

7. A medicament comprising a phage mixture according to claim 5.

8. The medicament according to claim 7, wherein said medicament further comprises an antibiotic that is active against gram-positive bacteria.

9. The medicament according to claim 7, wherein said medicament further comprises (i) an enzyme selected from the group consisting of lysins, proteases, peptidases, nucleases and glucosaminidases and/or (ii) a bacteriophage stabilizer selected from the group consisting of human serum albumin and $Mg^{2+}$ ions.

* * * * *